United States Patent [19]

Delledonne et al.

[11] Patent Number: 5,457,213

[45] Date of Patent: * Oct. 10, 1995

[54] CATALYTIC PROCEDURE FOR THE PREPARATION OF ORGANIC CARBONATES

[75] Inventors: Daniele Delledonne, Oleggio; Franco Rivetti, Milan; Ugo Romano, Vimercate, all of Italy

[73] Assignee: Enichem Synthesis S.p.A., Milan, Italy

[*] Notice: The portion of the term of this patent subsequent to Jun. 21, 2011, has been disclaimed.

[21] Appl. No.: 73,773

[22] Filed: Jun. 8, 1993

[30] Foreign Application Priority Data

Jun. 11, 1992 [IT] Italy ................. MI92A1432

[51] Int. Cl.$^6$ ................. C07D 317/36; C07C 69/96
[52] U.S. Cl. ................. 549/230; 558/277
[58] Field of Search ................. 549/230; 558/277

[56] References Cited

U.S. PATENT DOCUMENTS

| | | | |
|---|---|---|---|
| 5,151,541 | 9/1992 | Joerg et al. | 558/277 |
| 5,322,958 | 6/1994 | Dreoni et al. | 558/277 |

FOREIGN PATENT DOCUMENTS

| | | | |
|---|---|---|---|
| 0071286 | 2/1983 | European Pat. Off. | C07C 68/00 |
| 0413217 | 2/1991 | European Pat. Off. | C07C 68/00 |
| 0452997 | 10/1991 | European Pat. Off. | C07C 68/00 |
| 0463678 | 1/1992 | European Pat. Off. | C07C 68/00 |

OTHER PUBLICATIONS

Ellis, V. M. et al. "*Cobalt(II) Complexes of Some Pyridinecarboxylic Acids*" *J. Inorg. Nucl. Chem.* 1974, 36, 1031–1038.

*Primary Examiner*—Johann Richter
*Assistant Examiner*—Michael G. Ambrose
*Attorney, Agent, or Firm*—Rogers & Wells

[57] ABSTRACT

Catalytic procedure for the preparation of an organic carbonate having general formula (I):

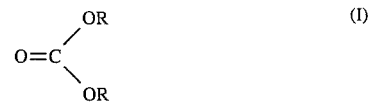

wherein R represents a $C_1$–$C_{10}$ alkyl radical, linear or branched, or a $C_5$–$C_8$ cycloalkyl radical; or of a cyclic organic carbonate having general formula (II):

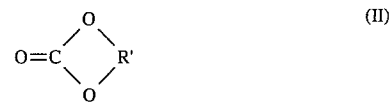

wherein R' represents a $C_2$–$C_5$ alkylene radical, linear or branched; including the reacting of an aliphatic or cycloaliphatic alcohol having general formula (III):

R—OH          (III)

or an aliphatic diol having general formula (IV):

HO—R'—OH          (IV)

wherein R and R' have the meaning described above, with carbon monoxide and oxygen, in the presence of a catalyst composed of a cobalt(II) or cobalt(III) ion and an organic binder containing at least one oxygen atom, characterized in that the process is carried out in the presence of at least one reaction coadjuvant selected from the following groups of linear or cyclic compounds: ureas, nitriles, amides, phosphoramides, sulphones, sulphoxides, carbamates.

21 Claims, 1 Drawing Sheet

CATALYTIC PROCEDURE FOR THE PREPARATION OF ORGANIC CARBONATES

The present invention relates to a catalytic procedure for the preparation of organic carbonates.

More specifically, the present invention relates to a catalytic procedure for the preparation of organic carbonates carried out in the presence of one or more reaction coadjuvants.

Organic carbonates are useful intermediates in the chemical field, and among these dimethyl carbonate is widely used as an additive for fuels, as an organic solvent and in the synthesis of other carbonates, both alkyl and aryl. In addition, organic carbonates can be used as synthetic lubricants, monomers for organic glass, plasticizers or as reagents in methylation and carbomethoxylation reactions for the preparation of phenol ethers, quaternary salts of ammonium, ureas, urethanes, isocyanates and polycarbonates.

The typical procedure for the preparation of alkyl carbonates consists in reacting an alcohol with phosgene, as described, for example, in Kirk-Othmer, "Encyclopedia of Chemical Technology", 3rd ed., No. 4, page 758. This procedure however has various technical problems (elimination of the hydrochloric acid produced in the reaction), as well as problems of safety deriving from the use of phosgene.

To overcome these disadvantages, alternative synthesis procedures have been proposed such as, for example, the oxidative carbonylation of methanol in the presence of catalysts based on palladium (U.S. Pat. No. 4,361,519; German patent 3.212.535 and English patent 2.148.881).

The disadvantages of this procedure basically consist in the high cost of the catalyst, the co-production of the esters of oxalic acid as described by Fenton in "Journal of Organic Chemistry" vol. 39, page 701, (1974) and in the negative effect of the co-produced water which, even in low concentrations, makes the catalyst ineffective.

Carbonylation catalysts based on compounds of copper have also been proposed (U.S. Pat. Nos. 3,846,468, 3,952,045, 4,218,391, 4,318,862, 4,360,477, 4,604,242 and 4,785,130), which cause problems however owing to the heterogeneity of the reaction system, a certain sensitivity of the co-produced water, which decreases both the selectivity of the carbon monoxide towards the formation of dimethyl carbonate and the rate of the reaction, and a high corrosiveness of the reaction medium.

More recently, according to what is described in Italian patent application 20809/A 90 and MI 91A 000374 filed by the Applicant, it has been found that dimethyl carbonate and other organic carbonates, also cyclic, can be prepared by operating in the presence of particular compounds of cobalt as carbonylation catalysts.

The Applicant has now found that, the addition of a reaction coadjuvant to the reactive system described in the above two Italian patent applications, surprisingly increases the productivity, the selectivity and the stability of the catalytic system.

The present invention therefore relates to a catalytic procedure for the preparation of an organic carbonate having general formula (I):

wherein R represents a $C_1$–$C_{10}$ akyl radical, linear or branched, or a $C_5$–$C_8$ cycloalkyl radical; or of a cyclic organic carbonate having general formula (II):

wherein R' represents a $C_2$–$C_5$ alkylene radical, linear or branched; including reacting an aliphatic or cyclo-aliphatic alcohol having general formula (III):

or an aliphatic diol having general formula (IV):

wherein R and R' have the meaning described above, with carbon monoxide and oxygen, in the presence of a catalyst composed of a cobalt(II) or cobalt(III) ion and an organic binder containing at least one oxygen atom, characterized in that the process is carried out in the presence of at least one reaction coadjuvant selected from the following groups of linear or cyclic compounds: ureas, nitriles, amides, phosphoramides, sulphones, sulphoxides, and carbamates.

More specifically, when an aliphatic or cyclo-aliphatic alcohol having general formula (III) is used in the carbonylation reaction, the procedure of the present invention can be schematized as follows:

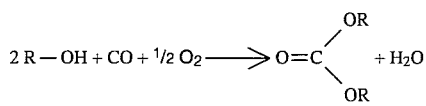

In the preferred embodiment the alcohol having general formula (III) is selected from methanol, ethanol, n-propanol, iso-propanol, n-butanol, iso-butanol, 2-ethylhexanol, and cyclohexanol, wherefor R in general formula (III) represents respectively the methyl, ethyl, n-propyl, iso-propyl, n-butyl, iso-butyl, 2-ethylhexyl, and cyclohexyl radical. In accordance with this, the organic carbonates having general formula (I) which are obtained are: dimethyl carbonate, diethyl carbonate, di-n-propyl carbonate, di-iso-propyl carbonate, di-n-butyl carbonate, di-iso-butyl carbonate, di-2-ethylhexyl carbonate, and di-cyclohexyl carbonate.

When an aliphatic diol having general formula (IV) is used in the carbonylation reaction, the procedure of the present invention can be schematized as follows:

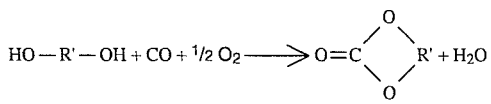

In the preferred embodiment the diol having general formula (IV) is ethylene glycol or propylene glycol and the cyclic organic carbonates having general formula (II) which are obtained have the following formula:

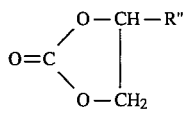

wherein R" represents hydrogen or methyl, respectively.

In the preferred embodiment, the procedure of the present invention is used in the preparation of dimethyl carbonate, diethyl carbonate and ethylene carbonate.

The catalyst used in the procedure of the present invention is preferably composed of a bivalent or trivalent cobalt ion and of an organic binder selected from those included in the following groups:

(a) binders of the carboxylate series;
(b) binders of the beta-diketonate series;
(c) binders of the series of Schiff bases having one or more oxygen atoms as functional groups, Schiff base referring to the condensation product of a primary amine with a carbonylic compound, as described, for example, by S. Dayagi and Y. Degani in "Methods of Formation of the Carbon-Nitrogen Double Bond", pages 61–130, in "The Chemistry of Functional Groups", Ed. S. Patai, Wiley-Interscience. This reaction can be represented as follows:

$$R^1R^2CO + R^3NH_2 \rightarrow R^1R^2C=NR^3 + H_2O$$

wherein $R^1$, $R^2$ and $R^3$ represent organic radicals;

(d) binders having a formula containing at least one pyridinic ring and having one or more functional groups of oxygen, as electron donors.

Examples of carboxylated organic binders belonging to class (a) which are suitable for the purpose can be represented with the following formulae:

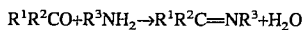

wherein $R_1$, $R_2$, $R_3$ or $R_4$ are monovalent, bivalent, trivalent or tetravalent organic radicals, respectively, containing up to 20 carbon atoms and which can additionally contain one or more non-carboxylic oxygen atoms, nitrogen atoms, sulphur atoms and halogens.

Examples of the above organic radicals are shown below:

$R_1$ can represent: H; $CH_3$—; $CH_3(CH_2)$—; $CH_3(CH_2)_2$—; $CH_3(CH_2)_3$—; $CH_2=CH$—; $(CH_3)_2CH$—; $(CH_3)_2CH$—$CH_2$—; $CH_3$—$CH$—$(CH_2)_4$—;

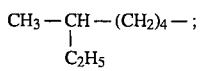

or cyclohexyl, phenyl radicals and phenyl substituted with $C_1$–$C_4$ alkyl, halogen, $C_1$–$C_4$ alkoxy, nitro, cyano;

$R_2$ can represent: —$CH_2$—; —$CH_2$—$CH_2$—; —$CH=CH$—; —$CH_2$—$CH_2$—$CH_2$—; —$CH_2$—$NH$—$CH_2$—$CH_2$—$NH$—$CH_2$—; —$CH_2$—$(CH_2)_2$—$NH$—$(CH_2)_2$—$CH_2$—; —$CH_2$—$(CH_2)_2$—$CH_2$—; —$CH(OH)$—$CH(OH)$—; or phenylene radicals, substituted phenylene radicals, a direct bond;

$R_3$ can represent:

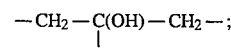

$R_4$ can represent:

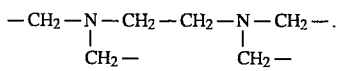

Examples of beta-diketonate binders belonging to class (b) suitable for the purpose can be represented by the following formula:

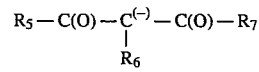

wherein $R_5$, $R_6$ and $R_7$, each independently, represent a hydrogen atom or an aliphatic, cyclo-aliphatic or aromatic radical containing up to 10 carbon atoms, and they can additionally contain one or more non-carbonylic oxygen atoms, nitrogen atoms, sulphur atoms and halogens. Among the beta-diketonates, acetylacetonate having the formula:

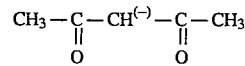

is particularly preferred.

Examples of Schiff base binders belonging to class (c) suitable for the purpose are those represented by the following formulae:

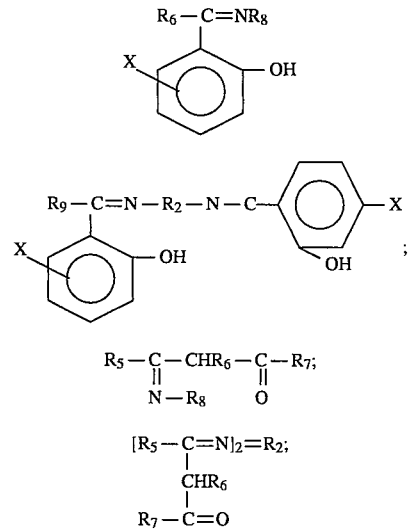

wherein $R_2$, $R_5$ $R_6$ and $R_7$ represent the groups described above, $R_8$ represents an aliphatic, cyclo-aliphatic or aromatic radical containing up to 10 carbon atoms, $R_9$ represents a hydrogen atom or has the same meaning as $R_8$ and X represents a $C_1$–$C_4$ alkyl radical, $C_1$–$C_4$ alkoxyl radical, a nitro, cyano, amine group or a halogen atom.

Examples of binders containing at least one pyridinic ring and having one or more functional groups of oxygen, belonging to class (d), can be represented by the following general formula:

Y—OH wherein Y represents a radical selected from:

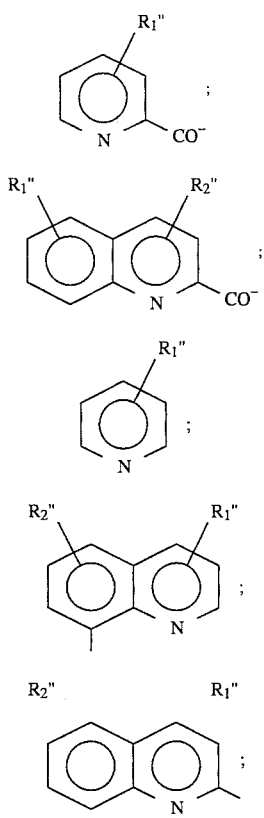

wherein $R"_1$ and $R"_2$ represent a hydrogen atom, a halogen atom such as, for example, chlorine, bromine or iodine, a $C_1$–$C_{20}$ alkyl or alkoxyl radical, a $C_6$–$C_{12}$ aryl radical or a $C_6$–$C_{12}$ hetero-aryl radical containing at least one heteroatom selected from nitrogen and oxygen.

In addition to the binders belonging to one or more of the above groups and cobalt, the catalyst may additionally contain a nitrogenous binder, either mono-dentate or polydentate such as, for example, pyridine, dipyridyl, phenanthroline, tetramethylethylendiamine and ethylendiamine, and/or a cation of an alkaline or earth alkaline metal such as, for example, sodium or barium.

Specific examples of catalysts used in the procedure of the present invention containing binders belonging to class (a) are the following: cobalt(II) acetate, $Co(CH_3COO)_2$; cobalt(III) acetate, $Co(CH_3COO)_3$; barium and cobalt(III) ethylendiamine tetra-acetate.

Specific examples of catalysts containing binders belonging to class (b) are: cobalt(II) acetylacetonate; cobalt (III) acetylacetonate; sodium and cobalt(II) acetylacetonate; cobalt(II) bipyridyl acetylacetonate; cobalt (II) phenanthroline acetylacetonate.

Specific examples of catalysts containing binders belonging to class (c) are:
[Co(SALEN)]$_2$, H$_2$O;

wherein SALEN represents:

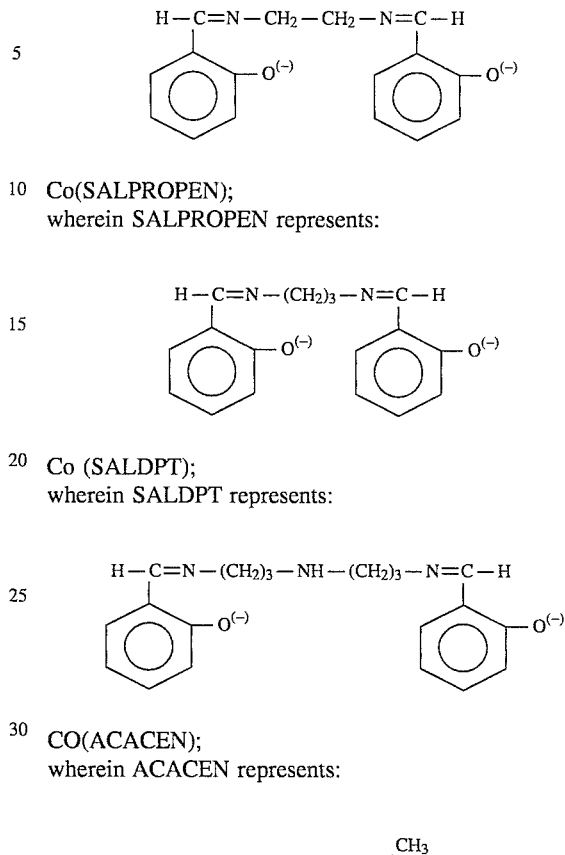

Co(SALPROPEN);
wherein SALPROPEN represents:

Co (SALDPT);
wherein SALDPT represents:

CO(ACACEN);
wherein ACACEN represents:

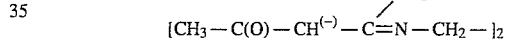

Co(SALOPH);
wherein SALOPH represents:

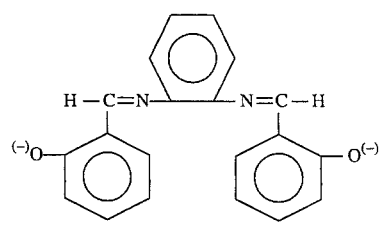

Specific examples of catalysts containing binders belonging to class (d) are:

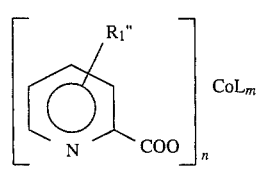

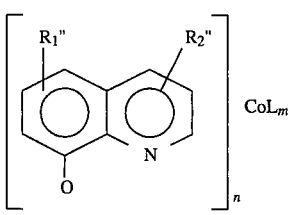

wherein:

n is a number between 1 and 3;

m is a number between 0 and 5;

$R_1''$ and $R_2''$, the same or different, have the meaning defined above;

L represents a secondary binder which can be a nitrogenous binder either mono or polydentate, neutral or anionic, such as for example pyridine, phenanthroline, piperidine, quinoline and isoquinoline, or an oxygenated binder, either mono or polydentate, such as for example, $H_2O$, —OH, —O—COO—$R_3''$ wherein $R_3''$ represents $C_1$–$C_5$ alkyl, —$OCH_3$ and $CH_3$—CO—CH(⁻)—CO—$CH_3$.

Examples of chelate complexes of cobalt with binders containing at least one pyridinic ring described above are:

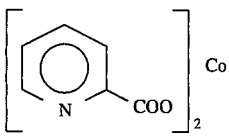

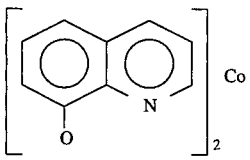

Catalysts containing binders belonging to class (d) are particularly active.

Reaction coadjuvants used in the procedure of the present invention can be selected from the following groups of compounds:

linear ureas having general formula (V):

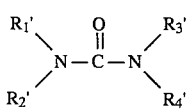

wherein $R_1'$, $R_2'$, $R_3'$ and $R_4'$ represent a hydrogen atom, $C_1$–$C_{20}$ alkyl, cyclo-alkyl, aryl or arylalkyl radicals, $C_1$–$C_{20}$ alkylene radicals or oxa-, azo- or thioalkylene radicals;

cyclic ureas having general formula (VI):

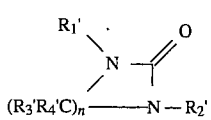

wherein $R'_1$, $R'_2$, $R'_3$ and $R'_4$ have the meaning defined above and n is 2 or 3.

nitriles having general formula (VII):

wherein $R_5'$ represents a $C_1$–$C_{10}$ alkyl, cyclo-alkyl, aryl or arylalkyl radical, oxa-, azo- or thioalkyl radical, or a $C_1$–$C_{10}$ alkylene radical and n is 1 or 2;

linear amides having general formula (VIII):

wherein $R_1'$, $R_2'$, and $R_3'$ have the meaning described above;

cyclic amides having general formula (IX):

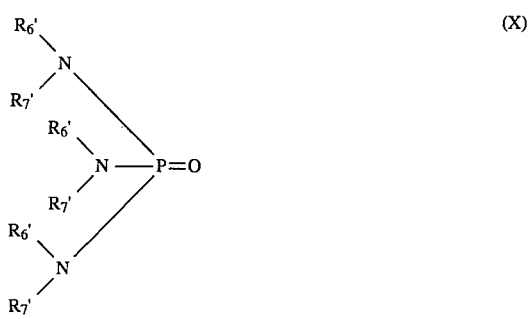

wherein $R_1'$, $R_2'$, and $R_3'$ have the meaning described above and n is a number between 3 and 7;

phosphoroamides having general formula (X):

wherein $R_6'$ and $R_7'$ represent a $C_1$–$C_{10}$ alkyl, cycloalkyl, aryl, arylalkyl, alkylene radical or oxa-, azo- or thioalkylene radical;

linear carbamates having general formula (XI):

wherein $R'_1$, $R'_5$ and $R'_6$ have the meaning described above;

cyclic carbamates having general formula (XII):

wherein $R_1'$, $R_2'$ and $R_3'$ have the meaning described above, n is 2 or 3;

linear sulphones or sulphoxides having general formula (XIII):

$$R_5'SO_mR_6' \qquad (XIII)$$

wherein $R_5'$ and $R_6'$ have the meaning defined above and m is 1 or 2;

cyclic sulphones or sulphoxides having general formula (XIV):

$(R_1'R_2'C)_nSO_m$ (XIV)

wherein $R_1'$, $R_2'$ and m have the meaning described above, n is 4 or 5.

Examples of reaction coadjuvants belonging to the group of ureas, linear or cyclic, having general formulae (V) and (VI) are:

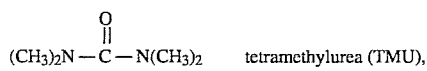
tetramethylurea (TMU),

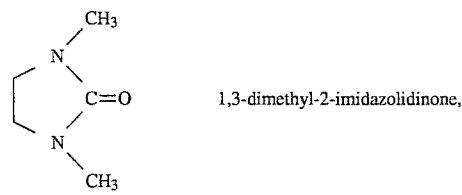
1,3-dimethyl-2-imidazolidinone,

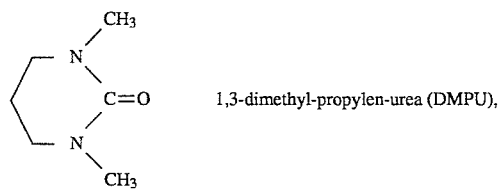
1,3-dimethyl-propylen-urea (DMPU), tetra-ethylurea (TEU), 1,3-dimethylenurea (DMEU), 1,3-dimethylurea, 1,3-diethylurea.

Examples of reaction coadjuvants belonging to the group of nitriles having general formula (VII) are: acetonitrile, propionitrile, butanonitrile, benzonitrile, phthalonitrile, terephthalonitrile, 1,4-dicyanobutane, succinonitrile, cyclohexylnitrile.

Examples of reaction coadjuvants belonging to the group of amides, linear or cyclic, having general formulae (VIII) and (IX) are:

$CH_3$—CO—$N(CH_3)_2$    N,N-dimethylacetamide
$HCON(CH_3)_2$ N,N-dimethylformamide,

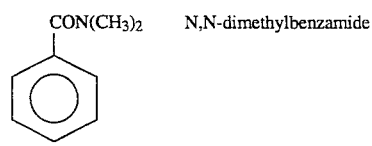
N,N-dimethylbenzamide

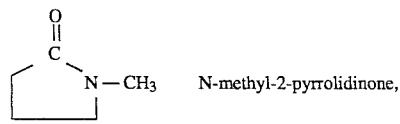
N-methyl-2-pyrrolidinone,

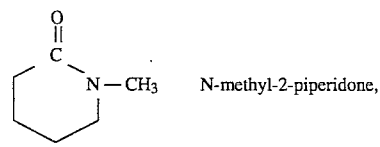
N-methyl-2-piperidone,

N-methylacetamide, N-methylformamide, N-methylbenzamide, 2-pyrrolidinone, ε-caprolactam, N-methyl-ε-caprolactam, 2-azocyclononanone, oxamide, malondiamide, bis(amide) of succinic acid.

Examples of reaction coadjuvants belonging to the group of phosphoramides having general formula (X) are: hexamethylphosphoramide (HMPA), hexaethylphosphoramide, tri(pentamethylen)phosphoramide, tri(oxapentamethylen)phosphoramide.

Examples of reaction coadjuvants belonging to the group of carbamates, linear or cyclic, are:

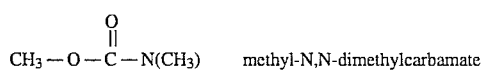
methyl-N,N-dimethylcarbamate

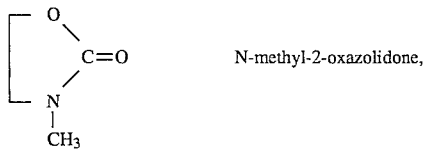
N-methyl-2-oxazolidone,

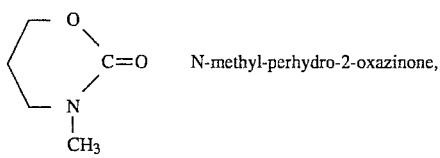
N-methyl-perhydro-2-oxazinone, methyl-N-ethylcarbamate, methyl-N-propylcarbamate, 2-oxazolidone, perhydro-2-oxazinone.

Finally, examples of reaction coadjuvants belonging to the group of sulphones or sulphoxides, linear or cyclic, having general formulae (XIII) and (XIV) are: dimethylsulphoxide, sulpholane.

In the procedure of the present invention, the reaction coadjuvants can be used individually or mixed with each other selecting them from one or more groups.

In the embodiment of the procedure of the present invention, a mixture is prepared between the preselected alcohol or diol with the preformed cobalt catalyst, or with the precursors of the catalyst, and the reaction coadjuvant. The above mixture, is brought into contact with carbon monoxide and oxygen operating at temperatures and pressures equal to or higher than atmospheric values.

The procedure is carried out in a liquid phase, at temperatures ranging from 25° C. to 200° C., preferably between 50° C. and 180° C., under a total pressure of carbon monoxide and oxygen of between atmospheric pressure and 100 Kg/cm$^2$, preferably between 2 and 100 Kg/cm$^2$, with a ratio in moles between the reaction coadjuvant and the alcohol of between 0.001:1 and 10:1, preferably between 0.01:1 and 2:1.

The ratio between the partial pressure of oxygen and carbon monoxide is generally between 0.005:1 and 50:1, preferably between 0.01:1 and 0.5:1.

Pure carbon monoxide can be used, or gaseous mixtures which contain carbon monoxide and one or more inert gases. Similarly pure oxygen can be used, or oxygen diluted with an inert gas, such as nitrogen, for example air or air enriched with oxygen.

The concentration of catalyst in the liquid reaction medium is generally between $1\times10^{-3}$ and 2 moles/liter.

The procedure of the present invention can be carried out either batchwise, or in continuous.

The separation of the reaction products can be carried out using the known techniques such as, for example, distillation and the catalyst can be recycled to the following reaction.

When the process is in continuous, the separation of the reaction products can also be carried out by evaporation caused by the saturation of the flow of gases fed into the reactor, following a similar procedure to that described in Italian patent application 20530/90 filed by the Applicant and illustrated below.

BRIEF DESCRIPTION OF THE DRAWINGS

To provide a better understanding of the practical embodiment of the procedure of the present invention.

Figure 1:
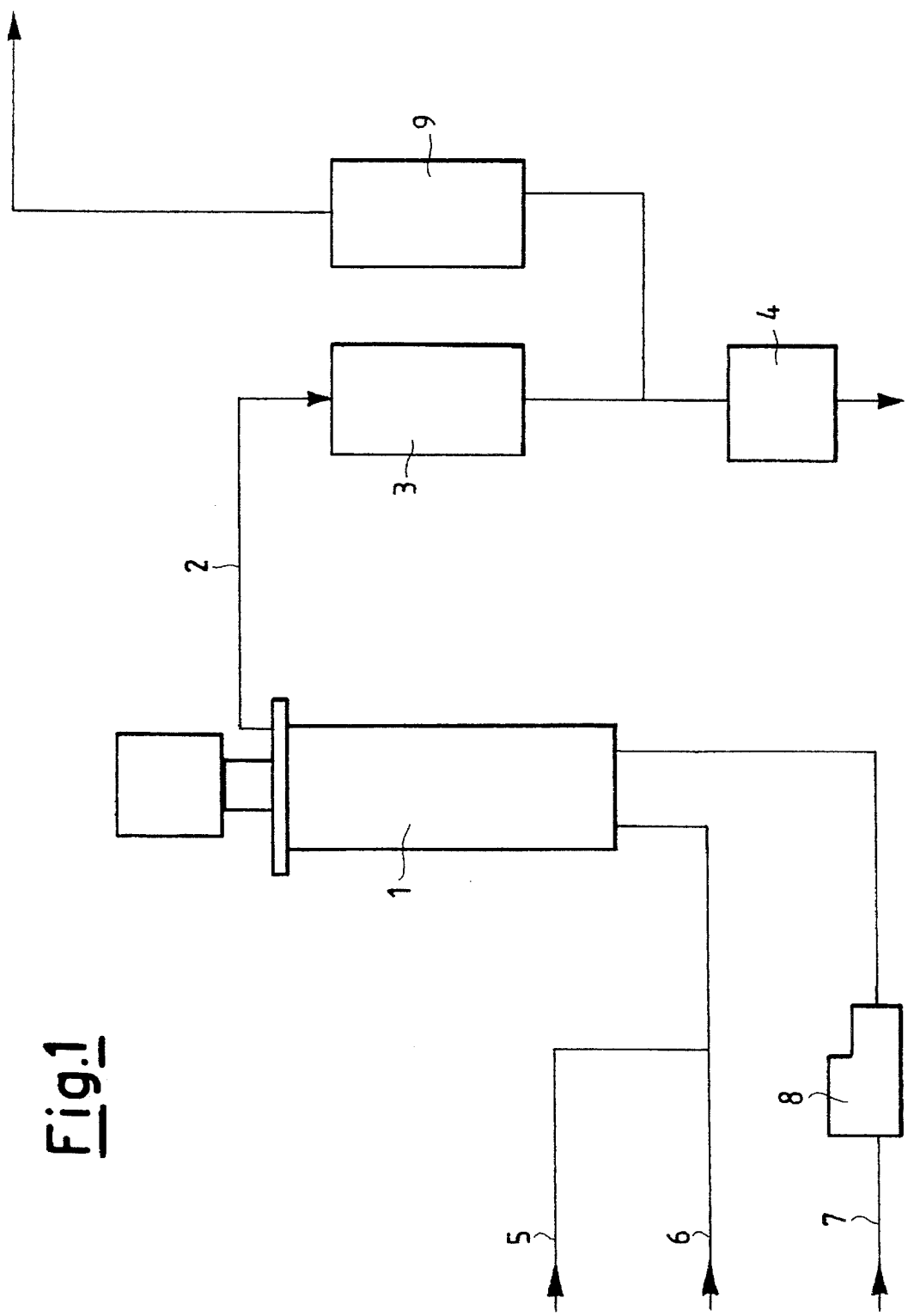
FIG. 1 shows an illustrative scheme which is not restricting of the equipment which is suitable for carrying out the present procedure.

The equipment is composed of a steel reactor (1), equipped with a mechanical stirrer and an external jacket in which a heating fluid circulates, an insulated vaporline (2) which connects the reactor (1) with a condenser (3) in which a cooling liquid circulates at a temperature of 5° C. The liquid condensed in (3) is collected in the tank (4), whereas the gases, after passing through a dry-ice trap (9), are partly discharged and partly recycled.

The feeding of the gases to the reactor (1) is carried out through lines (5) and (6) for the oxygen and carbon monoxide coming from the cylinders.

The liquid feeding of alcohol or glycol, is carried out through lines (7) by pump (8).

The following examples are illustrative and do not limit the present invention in any way.

EXAMPLE 1

Reactor (1), having a capacity of 500 ml, is charged with 150 ml of methanol, 3 ml of acetonitrile and 6 g of catalyst (tetrahydrate cobalt dipicolinate). The reactor is pressurized with carbon monoxide (line 6) at 30 Kg/cm$^2$ and is heated to 130° C.

When the pre-established operating conditions have been reached, the introduction of carbon monoxide (line 6), oxygen (line 5) and the liquid feeding (line 7) are initiated.

Under stationary conditions the flows are thus composed:

line 5: 3.4 Nl/hr of oxygen;

line 6: 81.6 Nl/hr of carbon monoxide;

line 7: 42 g/hr of a liquid flow composed of a mixture of methanol 98% and acetonitrile 2% (in volume).

The excess gas, saturated with reagent vapours and reaction products, is cooled in the condenser (3) and the condensed vapours are collected in the tank (4).

Under stationary conditions, 43.8 g/hr of condensate containing 3.8 g/hr of dimethyl carbonate are collected.

A productivity of 42 mmoles/hr of dimethyl carbonate is determined with a molar selectivity referring to the methanol of 90% and a conversion of methanol equal to 7.4%. The main by-product is composed of methyl formiate.

The reaction is kept for 41 hours without any decrease in productivity or selectivity of the catalyst being observed.

EXAMPLE 2

Reactor (1), having a capacity of 500 ml, is charged with 150 ml of methanol, 6 ml of acetonitrile and 9 g of catalyst (tetrahydrate cobalt dipicolinate). The reactor is pressurized with carbon monoxide (line 6) at 40 Kg/cm$^2$ and is heated to 130° C.

When the pre-established operating conditions have been reached, the introduction of carbon monoxide (line 6) oxygen (line 5) and the liquid feeding (line 7) are initiated.

Under stationary conditions the flows are thus composed:

line 5: 4.3 Nl/hr of oxygen;

line 6: 103.6 Nl/hr of carbon monoxide;

line 7: 40.5 g/hr of a liquid flow composed of a mixture of methanol 96% and acetonitrile 4% (in volume).

The excess gas, saturated with reagent vapours and reaction products, is cooled in the condenser (3) and the condensed vapours are collected in the tank (4).

Under stationary conditions, 41.5 g/hr of condensate containing 4.5 g/hr of dimethyl carbonate are collected.

A productivity of 50 mmoles/hr of dimethyl carbonate is determined with a molar selectivity referring to the methanol of 90% and a conversion of methanol equal to 9.1%. The main by-product is composed of methyl formiate.

The reaction is kept for 63.5 hours without any decrease in productivity or selectivity of the catalyst being observed.

EXAMPLE 3

Reactor (1), having a capacity of 500 ml, is charged with 150 ml of methanol, 10 g of N,N-dimethylacetamide and 9 g of catalyst (tetrahydrate cobalt dipicolinate). The reactor is pressurized with carbon monoxide (line 6) at 40 Kg/cm$^2$ and is heated to 130° C.

When the pre-established operating conditions have been reached, the introduction of carbon monoxide (line 6), oxygen (line 5) and the liquid feeding (line 7) are initiated.

Under stationary conditions the flows are thus composed:

line 5: 4.3 Nl/hr of oxygen;

line 6: 103.6 Nl/hr of carbon monoxide;

line 7: 38.8 g/hr of a liquid flow composed of a mixture of methanol 99.75% and N,N-dimethylacetamide 0.25% (in volume).

The excess gas, saturated with reagent vapours and reaction products, is cooled in the condenser (3) and the condensed vapours are collected in the tank (4).

Under stationary conditions, 41.5 g/hr of condensate containing 5.76 g/hr of dimethyl carbonate are collected.

A productivity of 64 mmoles/hr of dimethyl carbonate is determined with a molar selectivity referring to the methanol of 95% and a conversion of methanol equal to 11.1%. The main by-product is composed of methyl formiate.

The reaction is kept for 36 hours without any decrease in productivity or selectivity of the catalyst being observed.

EXAMPLE 4

Reactor (1), having a capacity of 500 ml, is charged with 150 ml of methanol, 10 g of tetramethylurea and 9 g of catalyst (tetrahydrate cobalt dipicolinate). The reactor is pressurized with carbon monoxide (line 6) at 40 Kg/cm$^2$ and is heated to 130° C.

When the pre-established operating conditions have been reached, the introduction of carbon monoxide (line 6), oxygen (line 5) and the liquid feeding (line 7) are initiated.

Under stationary conditions the flows are thus composed:

line 5: 4.3 Nl/hr of oxygen;

line 6: 103.6 Nl/hr of carbon monoxide;

line 7: 35.5 g/hr of a liquid flow composed of methanol 100% (in volume).

The excess gas, saturated with reagent vapours and reaction products, is cooled in the condenser (3) and the condensed vapours are collected in the tank (4).

Under stationary conditions, 39.5 g/hr of condensate containing 7.65 g/hr of dimethyl carbonate are collected.

A productivity of 85 mmoles/hr of dimethyl carbonate is determined with a molar selectivity referring to the methanol of 96% and a conversion of methanol equal to 16%. The main by-product is composed of methyl formiate.

EXAMPLE 5 (Comparative)

Reactor (1), having a capacity of 500 ml, is charged with 150 ml of methanol and 6 g of catalyst (tetrahydrate cobalt dipicolinate). The reactor is pressurized with carbon monoxide (line 6) at 30 Kg/cm$^2$ and is heated to 130° C.

When the pre-established operating conditions have been reached, the introduction of carbon monoxide (line 6), oxygen (line 5) and the liquid feeding (line 7) are initiated.

Under stationary conditions the flows are thus composed:

line 5: 3.2 Nl/hr of oxygen;

line 6: 76.8 Nl/hr of carbon monoxide;

line 7: 39.7 g/hr of a liquid flow composed of methanol 100% (in volume).

The excess gas, saturated with reagent vapours and reaction products, is cooled in the condenser (3) and the condensed vapours are collected in the tank (4).

Under stationary conditions, 40.6 g/hr of condensate containing 2.15 g/hr of dimethyl carbonate are collected.

A productivity of 24 mmoles/hr of dimethyl carbonate is determined with a molar selectivity referring to the methanol of 87% and a conversion of methanol equal to 4.4%. The main by-product is composed of methyl formiate.

Table 1 shows the selectivity, productivity and conversion values in relation to the reaction time.

It can be observed that, with the passing of time, there is a decrease in the productivity of dimethyl carbonate with a relative decrease in the conversion and selectivity.

TABLE 1

| Operating hours | Selectivity DMC/MeOH | Productivity mmoles/hr | Conversion MeOH % |
|---|---|---|---|
| 1–7   | 87% | 24 | 4.4 |
| 8–14  | 85% | 18 | 3.0 |
| 15–21 | 85% | 15 | 2.7 |
| 22–28 | 85% | 15 | 2.8 |
| 29–35 | 83% | 14 | 2.6 |

EXAMPLE 6

A 500 ml steel reactor equipped with a mechanical stirrer and heat-exchange device, is charged with 100 ml of methanol, 4.2 g of propionitrile and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 6.6 g (73 mmoles) is determined.

EXAMPLE 7

A 500 ml steel reactor equipped with a mechanical stirrer and heat-exchange device, is charged with 100 ml of methanol, 3.91 g of benzonitrile and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 7.0 g (78 mmoles) is determined.

EXAMPLE 8

A 500 ml steel reactor equipped with a mechanical stirrer and heat-exchange device, is charged with 100 ml of methanol, 4.81 g of 1,4-dicyanobenzene (or terephthalonitrile) and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 5.8 g (64 mmoles) is determined.

EXAMPLE 9

A 500 ml steel reactor equipped with a mechanical stirrer and heat-exchange device, is charged with 100 ml of methanol, 9.4 g of sulpholane and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 7.35 g (82 mmoles) is determined.

EXAMPLE 10

A 500 ml steel reactor equipped with a mechanical stirrer and heat-exchange device, is charged with 100 ml of methanol, 5.6 g of N,N-dimethylformamide and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 7.5 g (84 mmoles) is determined.

EXAMPLE 11

A 500 ml steel reactor equipped with a mechanical stirrer and heat-exchange device, is charged with 100 ml of methanol, 6.2 g of dimethylsulphoxide and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 9.7 g (108 mmoles) is determined.

EXAMPLE 12 (Comparative).

A 500 ml steel reactor equipped with a mechanical stirrer and heat-exchange device, is charged with 100 ml of methanol, and 4 g of catalyst (tetrahydrate cobalt dipicolinate). The reactor is pressurized at 30 Kg/cm$^2$ with a mixture of carbon monoxide and oxygen in a ratio of 2:1 at 130° C. for 90 minutes.

At the end of the reaction the reactor is cooled, the residuous pressure is discharged and the liquid is analysed by gas chromatography.

A yield of dimethyl carbonate equal to 5.3 g (59 mmoles) is determined.

We claim:

1. Catalytic procedure for the preparation of an organic carbonate having the general formula (I):

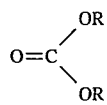  (I)

wherein R represents a $C_1$–$C_{10}$ akyl radical, linear or branched, or a $C_5$–$C_8$ cycloalkyl radical; or of a cyclic organic carbonate having the general formula (II):

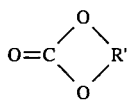  (II)

wherein R' represents a $C_2$–$C_5$ alkylene radical, linear or branched;
comprising reacting an aliphatic or cyclo-aliphatic alcohol having the general formula (III):

  (III)

or an aliphatic diol having the general formula (IV):

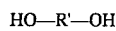  (IV), wherein R and R' have the meaning described above, with carbon monoxide and oxygen in the presence of a preformed catalyst composed of a cobalt (II) or cobalt (III) ion and an organic binder containing at least one oxygen atom or precursors of the preformed catalysts, characterized in that the process is carried out in the presence of at least one reaction coadjuvants selected from the group consisting of ureas, nitriles, amides, phosphoramides, sulphones, sulphoxides, and carbamates.

2. Procedure according to claim 1, wherein the alcohol having the general formula (III) is methanol, ethanol, n-propanol, iso-propanol, n-butanol, iso-butanol, 2-ethylhexanol, or cyclohexanol.

3. Procedure according to claim 1, wherein the diol having the general formula (IV) is ethylene glycol or propylene glycol.

4. Procedure according to claim 1, wherein the organic binder is selected from the group consisting of:
   a. binders of the carboxylate series;
   b. binders of the beta-diketonate series;
   c. binders of the series of Schiff bases having one or more oxygen atoms as functional groups; and
   d. binders having a formula containing at least one pyridinic ring and having one or more functional groups of oxygen as electron donors.

5. Procedure according to claim 1, wherein the reaction coadjuvants are selected from linear ureas having the general formula (V):

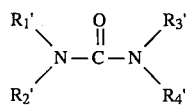  (V)

wherein $R_1'$, $R_2'$, $R_3'$ and $R_4'$ represent a hydrogen atom, a $C_1$–$C_{20}$ alkyl, cycloalkyl aryl or arylalkyl radical.

6. Procedure according to claim 1, wherein the reaction coadjuvants are selected from cyclic ureas having the general formula (VI):

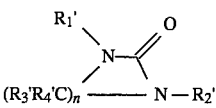  (VI)

wherein $R_1'$, $R_2'$, $R_3'$ and $R_4'$ represent a hydrogen atom, a $C_1$–$C_{20}$ alkyl, cycloalkyl, aryl, or arylalkyl radical and n is 2 or 3.

7. Procedure according to claim 1, wherein the reaction coadjuvants are selected from nitriles having the general formula (VII):

  (VII)

wherein $R_5'$ represents a $C_1$–$C_{10}$ alkyl, cycloalkyl, aryl or arylalkyl radical, optionally containing a heteroatom selected from the group consisting of oxygen, nitrogen, and sulfur and n is 1 or 2.

8. Procedure according to claim 1, wherein the reaction coadjuvants are selected from linear amides having the general formula (VIII):

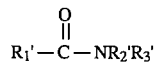  (VIII)

wherein $R_1'$, $R_2'$, and $R_3'$ represent a hydrogen atom, or a $C_1$–$C_{20}$ alkyl, cycloalkyl, aryl, or arylalkyl.

9. Procedure according to claim 1, wherein the reaction coadjuvants are selected from cyclic amides having the general formula (IX):

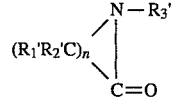  (IX)

wherein $R_1'$, $R_2'$, and $R_3'$ represent a hydrogen atom, or a $C_1$–$C_{20}$ alkyl, cycloalkyl, aryl, or arylalkyl radical, and n is a number between 3 and 7.

10. Procedure according to claim 1, wherein the reaction coadjuvants are selected from phosphoroamides having the general formula (X):

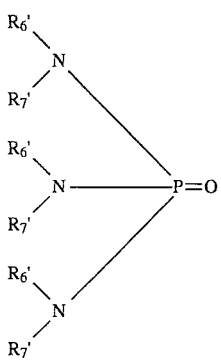 (X)

wherein $R_6'$ and $R_7'$ represent a $C_1$–$C_{10}$ alkyl, cycloalkyl, aryl, or arylalkyl radical.

11. Procedure according to claim 1, wherein the reaction coadjuvants are selected from linear carbamates having the general formula (XI):

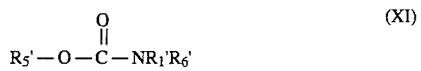 (XI)

wherein $R_1'$ represents a hydrogen atom or a $C_1$–$C_{20}$ alkyl, cycloalkyl, aryl or arylalkyl radical; $R_5'$ represents a $C_1$–$C_{20}$ alkyl, cycloalkyl, aryl or arylalkyl radical; $R_6'$ represents a $C_1$–$C_{10}$ alkyl, cycloalkyl, aryl, or arylalkyl radical.

12. Procedure according to claim 1, wherein the reaction coadjuvants are selected from cyclic carbamates having the general formula (XII):

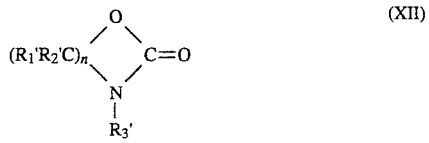 (XII)

wherein $R_1'$, $R_2'$ and $R_3'$ represent a hydrogen atom or a $C_1$–$C_{20}$ alkyl, cycloalkyl, aryl, or arylalkyl radical and n is 2 or 3.

13. Procedure according to claim 1, wherein the reaction coadjuvants are selected from linear sulphones or sulphoxides having the general formula XIII:

 (XIII)

wherein $R_5'$ represents a $C_1$–$C_{10}$ alkyl, cycloalkyl, aryl, or arylalkyl radical; $R_6'$ represents a $C_1$–$C_{10}$ alkyl, cycloalkyl, aryl, or arylalkyl radical; and m is 1 or 2.

14. Procedure according to claim 1, wherein the reaction coadjuvants are selected from cyclic sulphones or sulphoxides having the general formula (XIV):

 (XIV)

wherein $R_1'$ and $R_2'$ represent a hydrogen atom or a $C_1$–$C_{20}$ alkyl, cycloalkyl, aryl, arylalkyl radical and n is 4 or 5.

15. Procedure according to claim 1, wherein the reaction coadjuvants are mixed with each other and selected from one or more groups.

16. Procedure according to claim 1, wherein the preformed cobalt and organic binder catalyst or the precursors of the preformed catalyst and the reaction coadjuvant are mixed with the alcohol or the diol and the mixture is brought into contact with the carbon monoxide and the oxygen at temperatures and pressures equal or higher than atmospheric values.

17. Procedure according to claim 1 wherein the process is carried out in a liquid phase, at temperatures of between 25° C. and 200° C., under a total pressure of carbon monoxide and oxygen of between atmospheric pressure and 100 Kg/cm².

18. Procedure according to claim 1 wherein the ratio in moles between the reaction coadjuvant and the alcohol is between 0.001:1 and 10:1.

19. Procedure according to claim 1 wherein the ratio between the partial pressure of oxygen and carbon monoxide is between 0.005:1 and 50:1.

20. Procedure according to claim 1 wherein the concentration of the catalyst in the liquid reaction medium is generally between $1 \times 10^{-3}$ and 2 moles/liter.

21. Procedure according to claim 1 wherein the process is continuous and the separation of the reaction products can be carried out by evaporation caused by the saturation of the flow of gases fed into the reactor.

* * * * *